United States Patent [19]

Stolov

[11] 4,386,826
[45] Jun. 7, 1983

[54] ALPHANUMERIC DISPLAY WITH ELECTRONICALLY CONTROLLED COLORS

[76] Inventor: Michael Stolov, 25 Hapoel St., Nof-Yam, Israel

[21] Appl. No.: 185,738

[22] Filed: Sep. 10, 1980

[30] Foreign Application Priority Data

Sep. 10, 1979 [IL] Israel .................................. 58213

[51] Int. Cl.³ .............................................. G02F 1/13
[52] U.S. Cl. .................................... 350/345; 350/338
[58] Field of Search ................... 350/345, 338, 331 R

[56] References Cited

U.S. PATENT DOCUMENTS 3,674,341  7/1972  Hedman et al. ..................... 350/345
3,932,024  1/1976  Yaguchi et al. ..................... 350/338
4,196,973  4/1980  Hochstrate ....................... 350/345 X Primary Examiner—John K. Corbin
Assistant Examiner—Richard F. Gallivan
Attorney, Agent, or Firm—Fleit, Jacobson & Cohn

[57] ABSTRACT

A device for displaying any desired alphanumeric character in any desired color, comprising an arrangement of a transmissive liquid crystal display of a conventional pattern, for example of sixteen segments, behind which is placed a frosted glass, or translucent plastic, and a plurality of light sources of different colors, the light of which passes via the transmissive liquid crystal display, and a combination of a number of mirrors for increasing the brightness of the observation surface of the display.

7 Claims, 2 Drawing Figures

ALPHANUMERIC DISPLAY WITH ELECTRONICALLY CONTROLLED COLORS

STATE OF PRIOR ART

With the progress of color television, colored alphanumeric display on a television screen has been found useful, but not convenient in view of the large weight and large size of the color cathode-ray tube. Other means, such as cathodoluminescence devices are at present not sufficiently developed, because of the expected high price.

SUMMARY OF THE INVENTION

The present invention provides a possibility to produce flat and light-weight multicolor computer terminals, multicolor digital instruments and different multicolor indicating devices, wherein the change of the colors can be regulated for any desired level of brightness and can be applied for indicating any critical values or data.

DESCRIPTION OF THE PREFERRED EMBODIMENT

Figure 2:
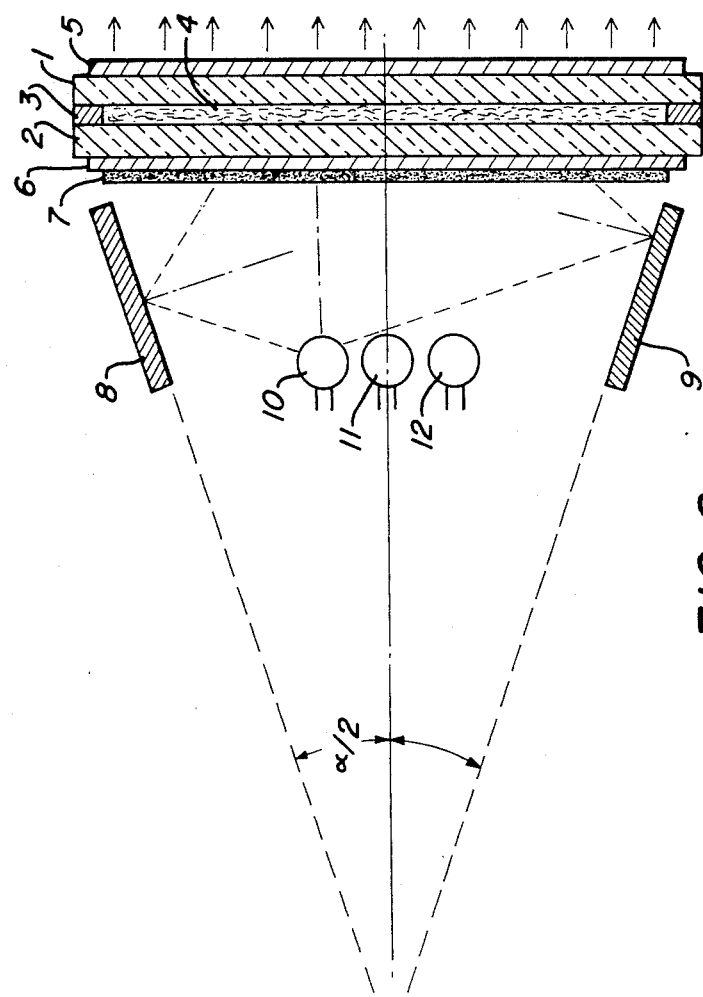
FIG. 2 is a cross-sectional view, generally along line A—A of FIG. 1, illustrating a multicolor display device, embodying the principles of the present invention.
Figure 1:
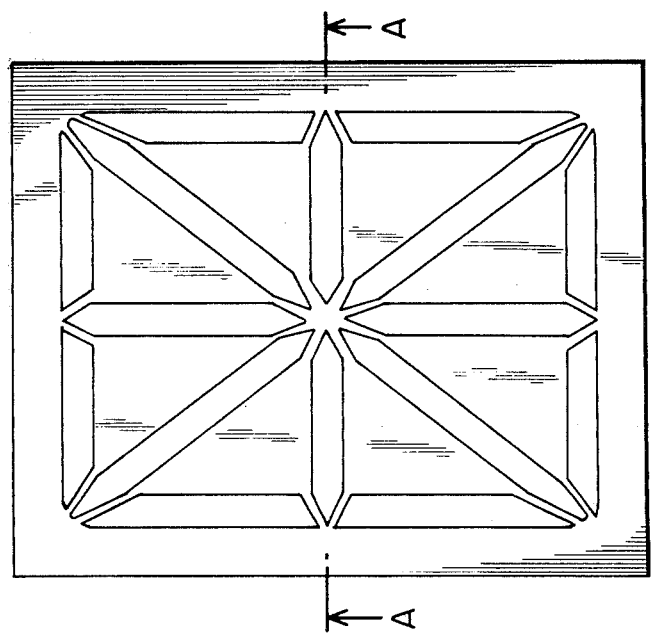
FIG. 1 is a front or rear view of a sixteen-segment pattern display, which according to the present invention can be utilized as a multicolor element of a flat computer terminal.

Referring to FIG. 2, there is schematically illustrated a multicolor display device embodying the principles of the present invention. The device includes a conventional field effect liquid crystal display, for example a transmissive sixteen segment type. The display device represented, comprises two glass plates 1 and 2, separated from each other by a frame 3, between which is disposed a liquid crystal 4. The front plate 1 and the rear plate 2, carry conventional electrodes and counterelectrodes and therefore, are not represented in FIG. 2. 5 and 6 are polarizers used in conventional transmissive liquid crystal displays. On the rear polarizator is glued on a scattering element 7, for example, a frosted glass or translucent plastic, or plastic with an uneven surface. Light sources 8, 9, and 10 of different colors are provided behind the liquid crystal panel. By activating simultaneously some of the electrodes of the liquid crystal display and one or several colored light sources, different alphanumeric characters in different colors, as desired, can be obtained. Unfortunately, a low efficiency of light output has been revealed in this arrangement. Sources of high consumption of energy were necessary to utilize, or by normal light sources to work with overrating currents, which has dramatically shortened the life-duration of the light sources. It was proved, that the addition of parabolic reflectors has not improved considerably the condition. By the addition of only two flat mirrors 8 and 9, a three times greater light output can be obtained. In this case, the angle between each mirror and the normal observation direction A—A, $\alpha/2$, should be smaller than 45°. It can be explained that in this case, there occurs a repeated reflection of the light beams in the space between the liquid crystal display and two mirrors, as it is shown in FIG. 2, with dotted lines. The observer looking through the liquid crystal display will see three lights instead of each single light source. The frosted glass makes the appearance of the plurality of lights look uniform. It allows to reduce considerably the distance between the light sources and liquid crystal rear surface, and this improved considerably the light efficiency and brightness of the device.

In the present invention there can be utilized different light sources, such as: fluorescent plasma or gas discharge tubes, cathodoluminescence sources, light emitting diodes and incandescent lamps.

The preferable colors are: Red, Green, Yellow, Blue, Pink, Violet.

With other colors can also be obtained good results, at least with only two light sources can be obtained three colors. For example, with the colors Red and Green can be obtained by mixing, an additional color-Yellow.

I claim:

1. A display device for displaying alphanumeric characters, and indication figures in any desired color, comprising in combination:
    a liquid crystal display means having polarizing means and a pair of opposed light transmissive plate means for displaying a desired pattern;
    a plurality of light sources of different colors for illunitating the said liquid crystal display means, said light sources being centrally disposed behind a first of said plate means;
    a number of flat mirrors disposed about said plurality of light sources, the edges of said mirrors being positioned close to the edges of said first plate means, at least two of said mirrors making an acute angle with respect to each other thereby making it possible to increase the illumination efficiency of the light sources;
    light diffusing means interposed between said first plate means and said light sources thereby causing a uniform light output by mixing of several light sources of different colors over the surface of said display means; and
    means for energizing predetermined parts of the liquid crystal display and simultaneously for energizing different colored light sources causing the energized pattern of the liquid crystal display to emit light in a desired color, according to the colors of the energized light sources.

2. The device of claim 1, wherein said light sources are of the fluorescent type or plasma type.

3. The device of claim 1, wherein said light sources are of the gas discharge type.

4. The device of claim 1, wherein said light sources are of the cathodoluminescence type.

5. The device of claim 1, wherein said light sources are of the light emitting diode type.

6. The device of claim 1, wherein said light sources are incandescent lamps of long life working at underrated currents.

7. The device of claim 1, wherein said light diffusing means comprises frosted glass, translucent plastic, or plastic with uneven light dispersing surface, and is glued to the rear polarizing means of the liquid crystal display means, or it is disposed at a small distance from the said rear polarizing means.

* * * * *